United States Patent
Huber et al.

[11] Patent Number: 5,904,833
[45] Date of Patent: *May 18, 1999

[54] METHOD AND APPARATUS FOR MEASURING THE CONTENT OF DISSOLVED CARBON DIOXIDE IN AN AQUEOUS MEDIUM

[76] Inventors: Calvin O. Huber, 709 W. Pioneer Rd., Mequon, Wis. 53092; George P. Olson, 2907 Fairview Ct., Waukesha, Wis. 53188

[*] Notice: This patent issued on a continued prosecution application filed under 37 CFR 1.53(d), and is subject to the twenty year patent term provisions of 35 U.S.C. 154(a)(2).

[21] Appl. No.: 08/704,284

[22] Filed: Aug. 28, 1996

[51] Int. Cl.⁶ .................................................. G01N 27/404
[52] U.S. Cl. .......................................... 205/783; 204/415
[58] Field of Search ........................ 204/415; 205/782.5, 205/783

[56] References Cited

U.S. PATENT DOCUMENTS

| | | | |
|---|---|---|---|
| 2,898,282 | 8/1959 | Flook et al. | 204/432 |
| 3,070,539 | 12/1962 | Arthur et al. | 204/415 |
| 3,718,567 | 2/1973 | Haddad | 204/415 |
| 3,869,354 | 3/1975 | Montalvo | 204/415 |
| 4,224,125 | 9/1980 | Nakamura et al. | 204/415 |
| 4,440,620 | 4/1984 | Ono et al. | 204/415 |
| 4,655,900 | 4/1987 | Neti et al. | 204/415 |
| 5,085,760 | 2/1992 | Razaq et al. | 204/431 |
| 5,558,756 | 9/1996 | Van Blaircom | 205/775 |

*Primary Examiner*—T. Tung
*Attorney, Agent, or Firm*—Andrus, Sceales, Starke & Sawall

[57] ABSTRACT

A method and apparatus for measuring the content of carbon dioxide in an aqueous medium, particularly boiler condensate from an electrical power plant. The apparatus comprises a container or housing defining an elongated vertical indicator chamber and a parallel vertical reference chamber which are connected by a generally horizontal passage. An indicator electrode and a reference electrode are mounted in the indicator chamber and reference chamber, respectively. The lower end of the indicator chamber is open, and the open end is enclosed by a membrane of microporous polytetrafluoroethylene. The lower end of the indicator electrode is flat or planar and is located in close proximity to the inner face of the membrane. A filling liquid consisting of pure water is located within both chambers in contact with the respective electrodes. The apparatus can be mounted in a condensate bleed line of a power plant. The condensate in the bleed line is in initially adjusted in pH to a value of about 4.5 and then is flowed in contact with the outer face of the membrane. Carbon dioxide in the condensate will diffuse through the membrane to provide a differential in electrical potential, which serves as a measurement of the carbon dioxide content.

10 Claims, 2 Drawing Sheets

METHOD AND APPARATUS FOR MEASURING THE CONTENT OF DISSOLVED CARBON DIOXIDE IN AN AQUEOUS MEDIUM

BACKGROUND OF THE INVENTION

In an electrical power plant utilizing steam operated turbines, a major portion of the steam condensate is recycled and reused to generate additional steam. The condensate can contain dissolved carbon dioxide and through the recycling, the carbon dioxide content can increase. It has been found that dissolved carbon dioxide can be corrosive to the turbines, as well as other metal components of the power plant. Also, dissolved carbon dioxide can contribute to scale accumulation which can decrease the thermal efficiency of heat exchange surfaces. Therefore, it is desirable to measure the carbon dioxide content in boiler condensate so that additional makeup water can be added to the condensate to maintain the carbon dioxide content within required limits.

It is recognized that the total carbonate species in an aqueous carbonate system can consist of carbon dioxide, bicarbonate, carbonate, and carbonic acid, and the equilibrium concentrations of the various carbonate species in aqueous solution are controlled by the pH of the solution. More specifically, at a pH below about 4.5, the carbonate species will consist entirely of carbonic acid. As the pH is increased to a value of about 8.5, the carbonic species will consist entirely of bicarbonate and as the pH is raised above 8.5, the predominant carbonate species will be carbonate.

Various devices have been employed in the past to measure the dissolved carbon dioxide content in an aqueous medium. One method of determining the carbon dioxide content is through bicarbonate titration, in which the pH of the water sample is initially adjusted to a value of 8.5, to convert the total carbonate to the bicarbonate form. The solution is then titrated to a pH of 4.5, converting the bicarbonate to carbonic acid, and the amount of titrating solution required to achieve this pH is a measure of the carbon dioxide content.

Differential titration is similar to bicarbonate titration, in that it relies on initial adjustment to a pH value of 8.5 to convert the total carbonate concentration to bicarbonate. The sample is then titrated to a pH of 5.0 to produce carbon dioxide, and the carbon dioxide is then removed from the sample by heating to the boiling point. The sample is then readjusted to the pH value of 8.5 and titrated to a pH of 5.0. The difference between the two titrations allows the total starting carbonate free of non-volatile acid/base interferences to be determined.

Another method that has been used to measure the free carbon dioxide present in an aqueous sample is direct titration. In contrast to the above two methods that measure the total carbonate concentration, this method only measures the free carbon dioxide present in the sample. The sample is titrated with sodium hydroxide to a pH of 8.5 to convert the total carbonate to sodium bicarbonate, and assumes the carbon dioxide is the only acidic species present in the sample.

Electrical conductivity can be used to measure the content of carbon dioxide in water, when carbonate species are the predominant anions, and the pH is confined to a narrow range. In this situation, the conductivity effectively monitors the carbonate concentration. However, the cell must be standardized with a reference solution of known conductivity to calculate a cell constant.

Another device that has been used commercially for monitoring carbon dioxide in condensate water at ppm levels is the Severinghaus type probe. This probe consists of a potentiometric glass pH probe and a thin layer of bicarbonate/sodium chloride filling solution is enclosed between the outer glass surface of the probe and a silicone rubber membrane. An internal reference electrode, which maintains its potential via the chloride content of the filling solution, is included. The analytical response in this probe is based upon the change in pH of the filling solution, due to carbon dioxide diffusion through the membrane into the thin layer of carbonate solution which produces a potentiometric signal.

A further device for measuring dissolved carbon dioxide based on potentiometry is the Scarano probe. In this probe, two electrodes of the same metal are utilized with a filling solution of pure water. A small relatively stable water layer is trapped between the working end of an indicator electrode and a gas permeable membrane formed of silicone rubber. Diffusion of carbon dioxide from the sample through the membrane to this water layer results in changes of surface pH at the electrode, and the change in metal surface oxidative potential resulting from the pH change determines the analytical signal.

While a number of devices for measuring the content of carbon dioxide in condensate have been utilized in the past, as described above, none of these devices have been capable of providing a rapid and stable response at sub-ppm levels, such as below 100 ppb.

SUMMARY OF THE INVENTION

The invention is directed to a method and apparatus for measuring the dissolved carbon dioxide content in an aqueous medium, and particularly in boiler condensate from an electrical power plant. The apparatus of the invention provides a stable and rapid response, and is capable of detecting limits of carbon dioxide below 100 ppb.

The apparatus of the invention includes a sealed container or housing that defines a pair of elongated vertical chambers, namely an indicator chamber and a reference chamber, which are connected through a generally horizontal passage. An indictor electrode and a reference electrode are mounted within the indicator chamber and reference chamber, respectively.

The lower end of the indicator chamber is open, and a membrane composed of microporous polytetrafluoroethylene is disposed across the open end of the chamber.

Located within both chambers, in contact with the respective electrodes, is a filling liquid which consists of pure water. The filling liquid only partially fills the indicator chamber and the reference chamber, leaving a headspace of air above the liquid level in the chambers. The lower end of the indicator electrode is flat or planar, and is disposed in close proximity to the inner face of the membrane, with a thin layer of the filling liquid being located within the space.

An annular trough or reservoir is formed within the indicator chamber and surrounds the indicator electrode. A quantity of a material which will react with carbon dioxide, such as a barium hydroxide aqueous solution, is located within the trough, and is exposed to the headspace in the indicator chamber.

The carbon dioxide sensing device of the invention has particular use in measuring the dissolved carbon dioxide content in boiler condensate. In this application of use, the apparatus can be connected in a condensate bleeder line and through suitable valving, a portion of the condensate is continually flowed through the bleeder line. The pH of the condensate in the bleeder line is initially adjusted to a value of about 4.5 by feeding an acidic material, such as citric acid, into the condensate. As the buffered condensate flows through the bleeder line, it will contact the outer face of the membrane of the sensing device and the microporous membrane will permit the diffusion of carbon dioxide through the membrane, but will prevent the diffusion of liquid. A relatively stable layer of water is trapped between the lower end of the indicator electrode and the inner face of the gas permeable membrane, and as carbon dioxide diffuses through the membrane, changes in carbon dioxide concentration in this thin water layer results in changes of surface pH at the electrode. The change in metal surface oxidative potential resulting from the pH change generates an analytic signal to provide an indication of the carbon dioxide content.

The reservoir of barium hydroxide solution will react with any carbon dioxide in the headspace of the indicator chamber to form an insoluble barium carbonate precipitate, thus removing any carbon dioxide from the headspace and enabling the apparatus to continually monitor the carbon dioxide content without any accumulation of carbon dioxide within the apparatus itself.

The device of the invention provides a continuous and rapid response to the carbon dioxide content and is capable of detecting carbon dioxide contents below 100 ppb. The device is of simple construction and requires minimal maintenance under field conditions.

DESCRIPTION OF THE DRAWINGS

The drawings illustrate the best mode presently contemplated of carrying out the invention.

In the drawings.

DESCRIPTION OF THE ILLUSTRATED EMBODIMENT

Figure 1:
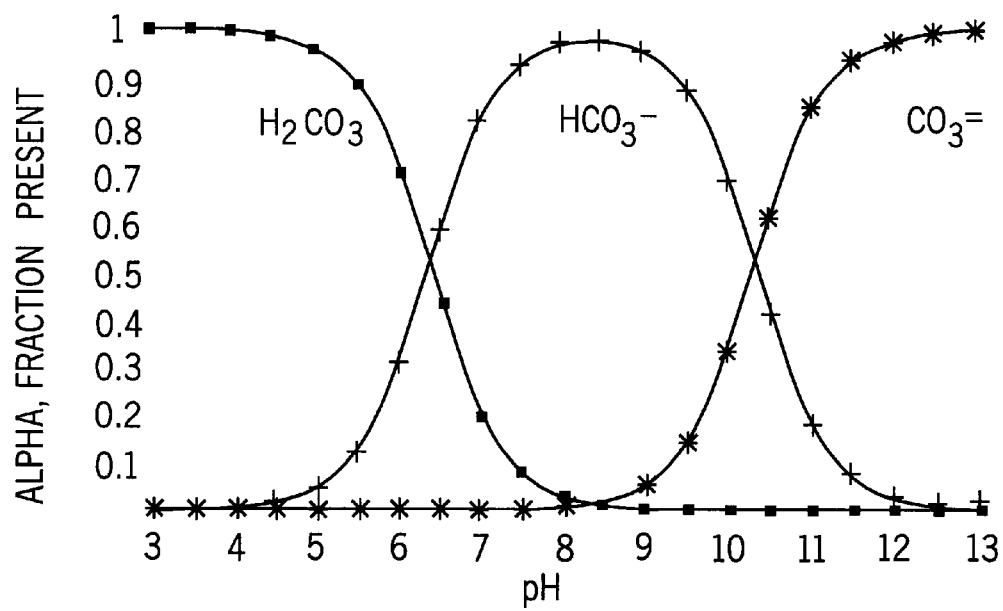
FIG. 1 is a graph showing the change in carbonate species in aqueous solution with a change in pH.

The generic term "total carbonate species" as hereinafter used, refers to the total concentration of carbon dioxide, bicarbonate, carbonate and carbonic acid in an aqueous system. The equilibrium conditions of the various carbonate species in aqueous solution are controlled by the pH of the solution, as shown in FIG. 1. More specifically, FIG. 1 shows the alpha fraction percent of the various carbonate species in aqueous solution with a change in pH. As can be seen from FIG. 1, at a pH below about 4.5, the carbonic species consists entirely of carbonic acid, with virtually no bicarbonate being present. As the pH is increased to a value of about 8.5 the carbonic acid content will decrease to appreciably zero, while the bicarbonate concentration increases to a maximum. A further increase of pH above 8.5, will cause an increase in the carbonate concentration, and a corresponding decrease in the bicarbonate concentration, as illustrated in FIG. 1.

Figure 2:
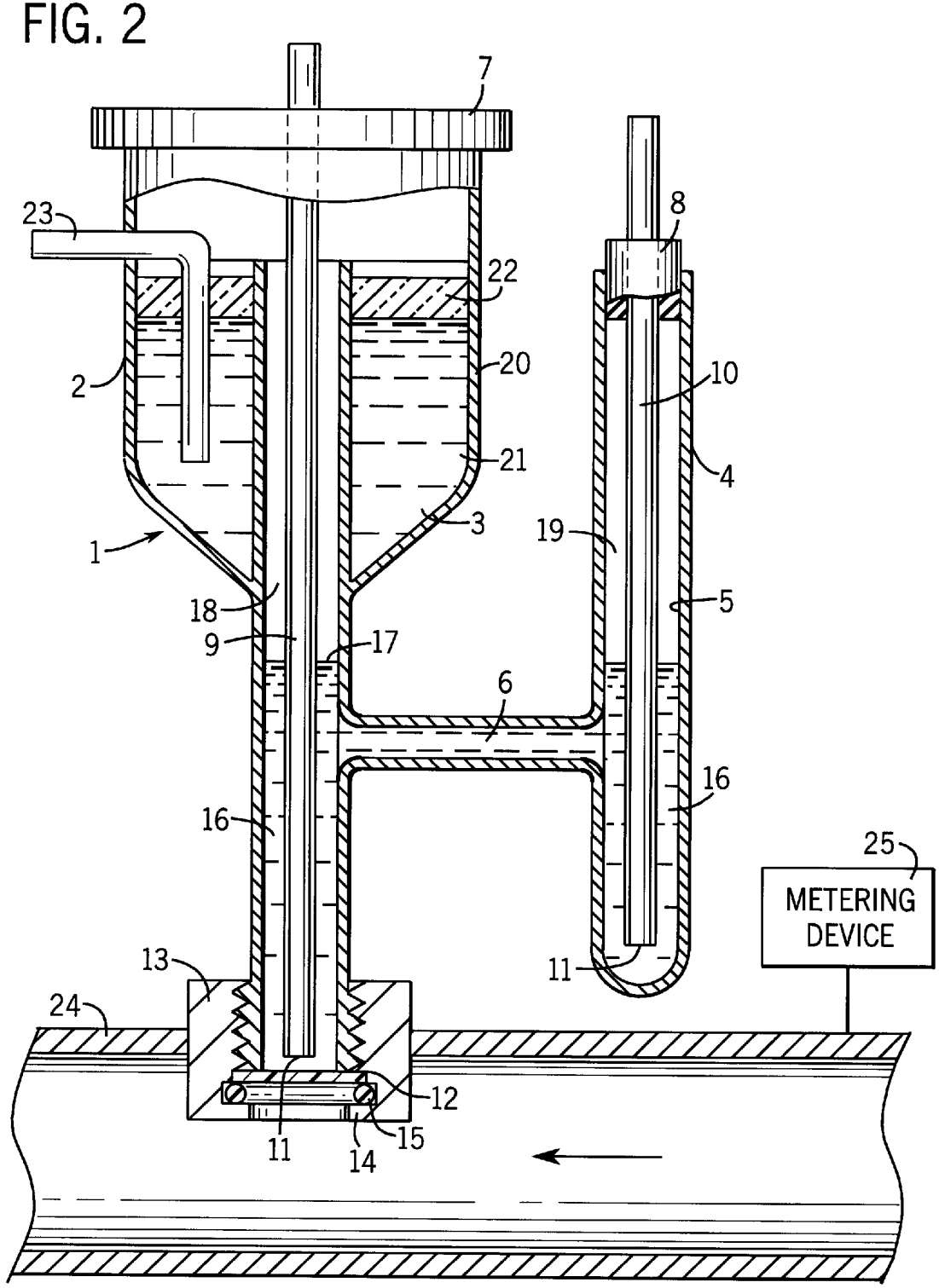
FIG. 2 is a longitudinal section of the apparatus of the invention as connected in a condensate bleeder line.

FIG. 2 illustrates the improved carbon dioxide sensor 1 of the invention. Sensor 1 preferably includes an indicator section 2, which defines a vertical elongated indicator chamber 3, and a reference section 4, which defines a vertical elongated reference chamber 5. Chambers 3 and 5 are connected by a generally horizontal connecting passage 6.

Both chambers 3 and 5 are sealed, and in this regard the upper end of chamber 3 is enclosed by a cap or closure 7, while the upper end of chamber 5 is sealed by a stopper or closure 8. The lower end of chamber 5 is also closed, as shown in the drawing, while the lower end of chamber 3 is open.

Mounted within chamber 3 is an indicator electrode 9 and a reference electrode 10 is mounted within the chamber 5. The upper ends of electrodes 9 and 10 extend in sealed relation through openings in the respective closures 7 and 8, and are adapted to be connected in an electronic circuit to suitable instrumentation, such as a high input impedance voltmeter or pH meter.

Electrodes 9 and 10 are composed of the same metal, preferably 300 series stainless steel, and have a diameter of about 0.06 inch. To provide uniformity between electrodes, the electrodes are preferably heat treated in an open furnace at a temperature of about 550° C. for 1 hour. The heating is then discontinued and the electrodes are retained in the oven until the temperature reaches 100° C., which is approximately 2½ hours, and the electrodes are then removed. Any scale produced by the heat treatment can be removed with steel wool.

The upper ends of the electrodes are then roughened, and the roughened areas can be covered with solder to provide a solder interconnection to the electronic circuit.

The outer surface of each electrode 9 and 10 is insulated by using a coating of epoxy resin covered by a sheet of heat shrink thermoplastic tubing. The lower bare metal flat ends 11 of the electrodes are preferably polished by using alumina to a finish of about 0.3 microns.

Positioned across the lower open end of indicator chamber 3 is a thin membrane 12 of microporous polytetrafluoroethylene. This material has the ability to provide gas diffusion therethrough, while preventing diffusion of liquids.

To hold the membrane 12 against the lower end of the indicator section 2, a cap 13 is threaded on the end of section 2 and the lower end of the cap is provided with an inwardly extending flange 14. A resilient O-ring 15 is positioned between flange 14 and the membrane 12. By threading down cap 13, the membrane 12 will be held tightly against the open lower end of indicator section 2.

As illustrated in FIG. 2, the lower flat or planar end 11 of electrode 9 is spaced slightly above the inner or upper face of membrane 12.

A quantity of pure water is used as the filling solution 16, and is located within the chambers 3 and 5, and the liquid level is indicated by 17. As the filling liquid does not completely fill the chambers 3 and 5, a headspace 18 is provided in chamber 3 above liquid level 17, and similarly a headspace 19 is provided in chamber 5 above the liquid level.

During operation, as will be hereinafter described, dissolved carbon dioxide in the condensate will pass through the membrane 12, and will be dissolved in the filling liquid 16. Over a period of time, the carbon dioxide will be evolved from the liquid into the headspaces 18 and 19, and the invention includes a provision for removing the carbon dioxide from the headspace 18. In this regard, the upper end of indicator section 2 is provided with an annular trough or reservoir 20, which contains a liquid 21 that will react with carbon dioxide to thereby remove the carbon dioxide from the headspace. The carbon dioxide scavenger 21 is preferably an aqueous solution of barium hydroxide, which will readily react with the carbon dioxide to produce insoluble barium carbonate, that will settle to the bottom of the trough 20. The barium hydroxide will remove the carbon dioxide from headspace 18 and produce a decreasing gradient of $CO_2$ in the filling liquid in chamber 3.

A layer of glass wool 22 can be applied to the upper surface of the liquid 21 to prevent the liquid 21 from entering the chamber 3 and possibly contaminating the filling liquid 16.

A suitable vent tube 23 can be connected to the trough 20 to equalize the pressure between the atmosphere and the interior of the chamber 3. As shown in FIG. 2, the lower end of the vertical leg of vent tube 23 is immersed in the liquid 21, while the horizontal leg of the vent tube is exposed to the atmosphere, The sensor of the invention can be used in a batch system to measure the carbon dioxide content of various bodies of water, but preferably the sensor is utilized to continually measure or monitor the carbon dioxide content in boiler condensate in power plant operation. In this regard, the sensor is mounted in a condensate bleeder line 24 that is connected to the main condensate line through a T-fitting. Suitable valving can be employed to continually feed a portion of the condensate through the bleeder line 24. Located upstream of the sensor 1 is a metering mechanism 25 for feeding an acidic material into the condensate to provide the condensate with a pH of about 4.5, as it flows past the sensor 1. Metering device 25 can be a conventional type and continuously meters an acidic material, preferably citric acid, into the condensate flowing within the bleeder line 24 at a pumping rate necessary to exceed the buffering requirement for carbon dioxide saturated water. In practice, about 5 ml per minute of citric acid can be injected into the line 24, to provide the condensate with a pH of about 4.5. Citric acid is preferred as the buffer, because it is non-volatile, and has a limited number of impurities. The presence of other volatile acidic species, such as acetic, sulfur dioxide and others, could lead to errors in measurement. It has been found that the use of citric acid for pH control will avoid the generation of hydrogen chloride or other active acidic species at the indicator electrode.

As the buffered condensate flows through line 26 past sensor 1, carbon dioxide dissolved in the condensate will diffuse through the membrane 12. A small, relatively stable film of water is trapped between the electrode end 11 and the inner surface of membrane 12. Changes in carbon dioxide concentration in this water film results in changes of surface potential at the electrode. The change in metal surface oxidative potential resulting from the pH change, will generate an analytical signal in the pH meter indicating the content of the carbon dioxide in the condensate.

The invention thus provides a rapid indication of carbon dioxide content in the sample, and is capable of detecting carbon dioxide limits below 100 ppb, thus permitting the sensor to meet the criteria needed for carbon dioxide monitoring in the power industry.

The barium hydroxide solution in trough 20 will remove the carbon dioxide from the unit and also isolates the electrodes from any atmospheric carbon dioxide.

We claim:

1. An apparatus for continuously measuring the carbon dioxide content in a flowing aqueous medium, comprising a housing defining a sealed chamber and having an opening therein, an indicator electrode mounted within the chamber, a reference electrode mounted in the chamber in spaced relation to said indicator electrode, a membrane composed of microporous polymeric material disposed across said opening and having a pair of opposed surfaces, said microporous polymeric material being permeable to the flow of carbon dioxide gas and impermeable to the flow of liquid, said indicator electrode having an electrode surface disposed in close proximity to a first of said surfaces of the membrane, a filling liquid consisting of pure water free of electrolytes disposed within the chamber in contact with said electrodes, means for continuously contacting a second of said surfaces with a flowing aqueous medium containing dissolved carbon dioxide, said carbon dioxide being diffused through said membrane into said chamber, means for measuring the electrical potential between said electrodes to provide an analytical signal indicting the content of carbon dioxide in said medium, said liquid only partially filling said chamber to provide a headspace in said chamber above the level of said liquid, and means for continuously removing carbon dioxide gas from said headspace while maintaining the sealed characteristics of said chamber.

2. The apparatus of claim 1, wherein said aqueous medium has a pH of about 4.5.

3. The apparatus of claim 1, wherein said indicator electrode has a flat end disposed in spaced parallel relation to said first surface of said membrane and a thin film of said liquid being disposed in the space between said flat end and said first surface.

4. The apparatus of claim 1, wherein said aqueous medium comprises boiler condensate from an electrical power plant.

5. The apparatus of claim 1, and including means for equalizing the pressure between said sealed chamber and the atmosphere.

6. An apparatus for measuring the carbon dioxide content in an aqueous medium, comprising a sealed housing defining a first chamber and a second chamber and having a passage connecting said chambers, an indicator electrode mounted in said first chamber, a reference electrode mounted in said second chamber, said first chamber having an opening therein, a membrane composed of microporous polytetrafluoroethylene disposed across said opening and having a pair of opposed surfaces, a filling liquid consisting of pure water disposed within said chambers in contact with said electrodes, said filling liquid only partially filling said chambers to provide a headspace in each chamber above the liquid level, an end of said indicator electrode disposed in closed proximity to a first of the surfaces of said membrane and a thin film of said liquid being disposed in the space between said end and said first surface, means for contacting a second of said surfaces of the membrane with an aqueous medium containing dissolved carbon dioxide, said carbon dioxide being diffused through said membrane and into said film of liquid, means for measuring the electrical potential between said electrodes to provide an analytical signal indicating the content of said carbon dioxide in said medium, means for continuously removing carbon dioxide from the headspace of said first chamber and comprising an annular trough disposed in said first chamber and surrounding said indicator electrode, and a quantity of an aqueous solution of barium hydroxide disposed in said trough and exposed to said headspace, carbon dioxide gas in said headspace reacting with said barium hydroxide to thereby remove carbon dioxide from said headspace.

7. A method of continuously measuring the carbon dioxide content in a flowing liquid, comprising the steps of mounting an indicator electrode and a reference electrode in spaced relation in a sealed chamber, said chamber having an opening therein located adjacent an end of said indicator electrode, disposing a membrane of microporous polymeric material across said opening with an inner surface of said membrane being in close proximity to said end of the indicator electrode, introducing a quantity of pure water into the chamber in contact with said electrodes to partially fill the chamber and provide a headspace above the level of the water, continuously contacting an outer surface of said membrane with a flowing liquid containing dissolved carbon dioxide, connecting the electrodes in an electronic circuit, measuring the difference in potential between said electrodes to provide an analytical signal corresponding to the content of carbon dioxide in said liquid, and continuously removing gaseous carbon dioxide from said headspace while maintaining the sealed characteristics of said chamber.

8. The method of claim 7, and including the step of adjusting the pH of said flowing liquid to a value of about 4.5 before contacting the outer surface of the membrane with said flowing liquid.

9. The method of claim 7, wherein the liquid is boiler condensate from an electrical power plant.

10. The method of claim 7, wherein the step of removing gaseous carbon dioxide comprises exposing the gaseous carbon dioxide to an aqueous solution of a material capable of chemically reacting with carbon dioxide, and reacting said carbon dioxide with said material to form an insoluble compound.

* * * * *